United States Patent [19]

Fleckenstein et al.

[11] 4,108,163

[45] Aug. 22, 1978

[54] PUNCTURE PROBE FOR MEASURING HEAT TRANSFER OR BLOOD CIRCULATION OF LIVING TISSUES

[75] Inventors: Wolfgang Fleckenstein; Volker Thiemann, both of Kiel, Germany

[73] Assignee: Drägerwerk, Aktiengesellschaft, Lübeck, Germany

[21] Appl. No.: 738,826

[22] Filed: Nov. 4, 1976

[30] Foreign Application Priority Data

Nov. 5, 1975 [DE] Fed. Rep. of Germany ....... 2549559

[51] Int. Cl.² .............................................. A61B 5/00
[52] U.S. Cl. ................................. 128/2 H; 73/359 R; 128/2.05 F
[58] Field of Search ............. 128/2 H, 2.05 F, 2.05 V; 73/359, 361

[56] References Cited

U.S. PATENT DOCUMENTS 2,816,997  12/1957  Conrad ............................ 128/2 H X

FOREIGN PATENT DOCUMENTS 1,907,150  9/1969  Fed. Rep. of Germany.
2,247,962  9/1972  Fed. Rep. of Germany.

*Primary Examiner*—Kyle L. Howell
*Attorney, Agent, or Firm*—McGlew and Tuttle

[57] ABSTRACT

A puncture probe, comprises a probe support having an end with a probe surface with a plurality of alternately arranged layers of thermoelectric conductive material and insulation formed around said probe support adjacent the probe surface or covering a portion or all of it. At least two pairs of the conductive material layers are in contact at locations which are distinct from each other and they are made of thermoelectric conductive material and form thermocouples, one of these thermocouples being heated either by electric energy of by light energy. The probe surface may be planar at the end and a central portion may be covered by a layer of the insulation. In addition, a conductor film forming an inside covering layer on the probe support may be arranged to join or contact a separate conductive layer which extends downwardly on the outside of an insulation layer into contact with the probe surface. Additional outside layers applied over the first two insulation separated layers are advantageously formed with an inward depression at the location of the probe surface. The probe support surface may include a shaft tube with an inorganic fiber tip.

11 Claims, 4 Drawing Figures

PUNCTURE PROBE FOR MEASURING HEAT TRANSFER OR BLOOD CIRCULATION OF LIVING TISSUES

FIELD AND BACKGROUND OF THE INVENTION

This invention relates in general to the construction of probes for measuring heat transfer of blood circulation of living tissues and, in particular, to a new and useful probe, including a probe support having a plurality of alternately arranged layers of thermoelectric conductor material and insulation formed around the support and forming two oppositely connected thermocouples, each including an outwardly extending layer of a thermoelectric material and a common connecting layer of another thermoelectric material, one of which is heated and arranged in the range of the probe tip or surface, and the other is unheated and arranged at a spaced location from the probe tip.

DESCRIPTION OF THE PRIOR ART

Probes for measuring conditions of human tissue are known from German Pat. No. 956,868, from the book "Durchblutungsmessung mit Waermeleitelmenten" (Blood circulation measurements with heat conductive elements), by Golenhofen, Hensel and Hildebrants, Published by Georg Thieme, Stuttgart (1963), and from DAS No. 1,121,274. These probes are usually arranged inside metal tubes which impart mechanical stability to the probe and enclose them tightly.

The individual thermocouple legs, as well as the heating current leads are designed as thin wires insulated from each other by glass, etc. The heating is effected by Peltier heating, heating with resistance wires or, as in the case of the last-mentioned publication, by diathermal heating of the tissue surrounding the tip of the probe.

A disadvantage of these constructions is the large diameter of the probe tip, which is due to the design, and which limits the spatial resolution of the measurement to such an extent that the measurement of microcirculation is impossible, and only mean values of the blood circulation in large tissue sections can be measured. Micro-circulation is, however, of great interest to the physician. Another disadvantage of the known probes is the great mass of the probe tip, which leads to a high thermal capacity, and thus, to a longer response time of the probe. A further disadvantage is the very great thermal conductivity of the probe, which requires a large spacing between the two thermocouples to avoid heating of the unheated thermocouple. This great spacing leads to a great dependence of the measured value on temperature gradients in the tissue, for example, on organ surfaces. An attempt to improve the known probes by reducing the wire thicknesses and by weakening the supporting structure led to probes which no longer had sufficient mechanical stability.

SUMMARY OF THE INVENTION

The present invention provides a probe which permits maximum spatial resolution with mechanical stability, and a short response time without heating the unheated thermocouple.

According to the invention, the outwardly extending leg or layer of the thermocouple in the range of the probe tip, and the connecting leg or layer are arranged as thin films, separated by insulating thin films except for a contact zone, superposed on the surface of an electrically and thermally insulating pointed supporting body. On the shaft region of the probe, the connecting leg or layer is contacted with the outwardly extending leg or layer of a second thermocouple, designed as a thin film.

With the present state of thin film technique, it is possible to apply thin films of high mechanical stability on very thin, highly stable support needles, for example, of glass. Probes with a tip diameter of the order of 1 $\mu$ can be readily produced. Probes with this tip volume have such a low thermal capacity that the response time can be brought into the range of the rise time of the required amplifiers. The heating of the unheated thermocouple by the heated thermocouple is effected substantially by thermal conduction in the probe and by thermal conduction in the tissue. The thermal conduction in the probe is very small, however, due to the extremely high ratios of the surface to the volume, since the probe is already in thermal equilibrium with the tissue in a small distance from the heated point. Thermal conduction through the tissue likewise does not lead to measurable co-heating, since the necessary filament power is extremely low due to the low thermal capacity. The two thermocouples can therefore be arranged in an extremely small space of a few 100 $\mu$. This space is sufficiently small, related to the temperature gradients appearing in the tissue. The spatial resolution of the probe, according to the invention, is excellent, since the temperature field around the probe tip is only a few $\mu^3$, and the accuracy of the measurement is thus in this range. The probe according to the invention permits maximum three-dimensioned resolution of the blood circulation profiles of organs. The invention, for the first time, provides information about the vascularization and extent of blood circulation in the range of the smallest blood vessels. Vascular diseases and organic diseases, which manifest themselves mainly in the range of the smallest vessels, can be determined in this way. Furthermore, blood circulation profiles of large vessels can be made, particularly, for intra-operative diagnosis.

From DOS No. 1,907,150, it is also known to design thermocouple legs or layers in layered construction. In this arrangement, the insulation is effected by geometric separation of the legs on different sides of an insulating supporting body. DOS No. 2,247,962 shows a thermocouple where the legs are made of semiconductor material and are separated by a thin layer. Miniaturization of the constructions known from these publications to the desired extent is not possible, however, so that these suggestions have not found their way into the above cited state of the art.

The probe according to the invention is further advantageously characterized by the fact that the heating is effected by a resistance film, insulated from the legs by insulating thin films, and arranged in the range of the heated thermocouple. The resistance thin film is separated from the thermocouple only by a very thin insulating thin film, and it thus brings the filament power into the proximity of the thermocouple to be heated. But it contributes very little to the thermal capacity of the tip.

The probe according to the invention is additionally advantageously characterized by the fact that the resistance thin film is contacted on an extremely small area with a conductor thin film carrying the heating current which is electrically insulated from the legs or layers and the resistance thin film by insulating thin films, this area being inside the ring-shaped heated thermocouple. In this design, the current flows between the very small contact surface of the feeder conductor with the resistance film in diverging current paths through the resistance thin film for its connecting contacting, so that the maximum current density and, thus, the maximum filament power appears on the thermocouple. In this way, the necessary total filament power is reduced and is concentrated exactly to the desired operation.

Another advantageous feature of the invention is the fact that two additional thin films of different thermoelectric materials, insulated by insulating thin films, are contacted with the heated thermocouple in a mutual type thermocouple. This alternate design of the heating system as a mutual type thermocouple permits particularly simple, layered construction of layers of only two materials, whose common contacting in the tip range can be produced very easily. In this case, the filament power is generated directly in the thermocouple.

The probe of the invention further advantageously is characterized by the fact that the support is designed for radiant heating of the heated zone as a photoconductor whose surface is designed as a reflecting surface, with the exception of a window arranged in the zone to be heated. Radiant heating prevents, a priori, any electrical influence of the heating current on the thermoelectric voltage, as it can occur in electrical heating. The highly constant radiation source can be readily provided at the shaft end of the probe, and the heating takes place only in the desired zone in which the radiation issues from the interior of the support. The absorption can take place with advantage in the layered structure above the window, so that a constant absorption is ensured. The absorption can also take place in a radiation-transmissive layered structure, or in the absence of a layered structure above the window, in the absorbent tissue. The radiation issues here into a space sector of the tissue which is heated down to a certain depth of penetration. The filament power is generated exactly concentrated directly in the tissue and need not be transferred from a heating system to the tissue.

The probe according to the invention with electric heating of the tissue by two electrodes, of which one is very small and arranged in the zone to be heated, and which corresponds to the design of DAS No. 1,121,274 is advantageously characterized by the fact that the small electrode is provided as an exposed panel of a conductor thin film arranged on the probe, insulatingly covered on the outside, while the other larger electrode is arranged as an outside conductor thin film on the shaft zone of the probe. The advantages of electric heating can thus be obtained with a probe of simple design, according to the invention. The small electrode can be formed without additional layers by an exposed panel of the outside thermocouple leg or layer, and with DC heating, the differentiation of the thermoelectric DC voltage from the AC interference signal can be effected in a simple manner in the measuring amplifier. The electric heat is generated again, directly in the tissue, at the point where the current path has the smallest cross-section, namely, directly in front of the small electrode. The resistance of the current path, and thus the filament power, is independent of the movements of the probe, due to the fixed geometric design.

Furthermore, the probe according to the invention is further characterized by the fact that the support is designed as a fiber or bundle of fibers set or grown in the shaft zone. With this design of the probe, it is possible to achieve extremely thin probe tips of extremely great strength, if, for example, monocrystalline or polycrystalline inorganic fibers or fiber bundles are used.

Finally, the probe according to the invention, is characterized by the fact that at least the heated zone of the probe is coated with a film of low thermal conductivity. The heated zone is thus thermally screened from the medium, so that the desired excess temperature of the heated zone can be maintained with a lower filament power. This coat also serves as corrosion protection with a suitable selection of the material.

Accordingly, it is an object of the invention to provide a probe for measuring heat transfer or blood circulation of living tissues, which comprises, a probe support which has a shaft portion and an end tip with a probe surface and which has a plurality of alternately arranged layers or legs of thermoelectric conductive material and insulation formed thereon adjacent said probe surface, and including two pairs of said conductor material being in contact at locations spaced from each other and forming thermocouples with one of the conductive layers being heated and arranged in the area of the probe tip, and the other being unheated and arranged in the range of the probe shaft.

A further object of the invention is to provide a probe for measuring heat transfer or blood circulation of living tissues, which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawing and descriptive matter in which there are illustrated preferred embodiments of the invention.

DESCRIPTION OF THE PREFERRED EMBODIMENTS

Figure 1:
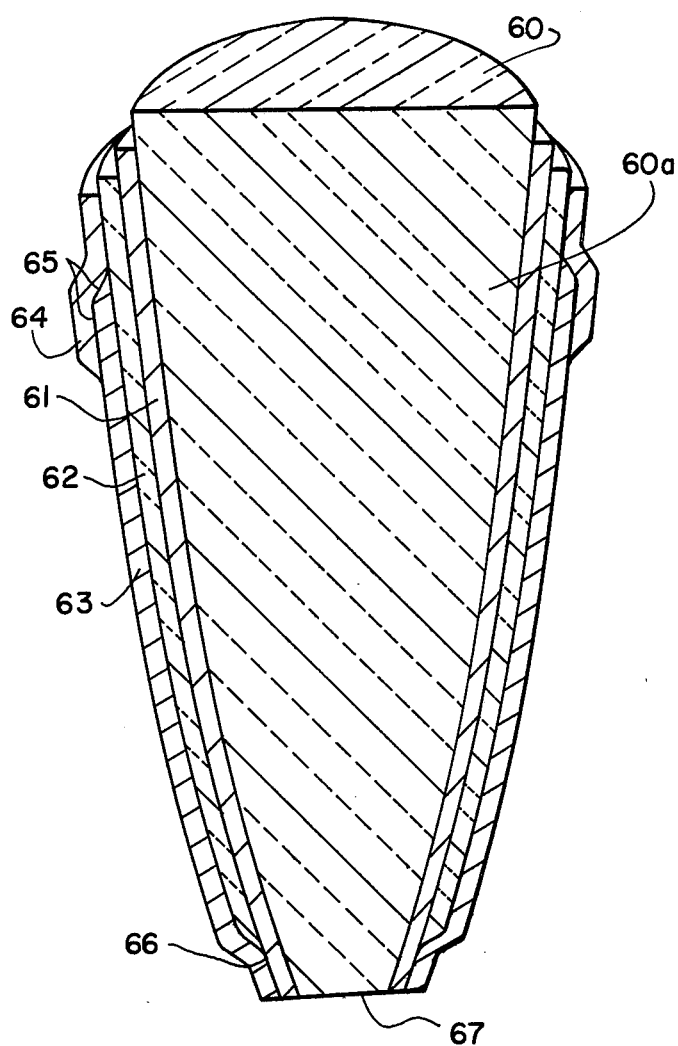
FIG. 1 is a cross-sectional view of a probe having radiant heating of the tissues and constructed in accordance with the invention.

Referring to the drawings in particular, the invention embodied therein in FIG. 1 comprises a probe, which includes an electrically and thermally insulated support 60 having a plurality of films disposed over the side walls thereof in a shaft portion 60a at a location adjacent to a probe tip having a probe tip surface 67. In accordance with the invention, the plurality of layers or films include a conductive film 61 which extends from the inside to the outside of the probe and an insulating film 62 extending over the conductive film 61. A second conductive film 63 is applied over the insulating film 62. Conductive films 61 and 63 are superposed in the range of the probe tip adjacent surface 67 at a location where the insulating film 62 is discontinued, so that they are in direct electrical contact and form a first thermocouple 66. Conductive film 63 ends in a zone along the probe shaft portion 60a and forms a second thermocouple 65 in a contact area with an outer conductor film 64. The end of conductor film 63 is several 100 μ behind the tip surface 67 and it is contacted there by the adjoining third conductor film 64. Thermocouple 65 is formed between the film 63 and 64. Conductor films 64 and 61 comprise the same thermoelectric material and they form two outwardly extending legs of the thermocouples 65 and 66, respectively. Conductor film 63 in between comprises a different thermoelectric material and forms a connecting leg of the two thermocouples 65 and 66. Thermocouple 66 in the probe tip is thus oppositely connected to thermocouple 65, so that the difference of the two thermoelectric voltages can be tapped at the outwardly extending legs formed by films 61 and 64.

Support 60 is advantageously made of a material, such as glass, which is also suitable as a support for the other embodiments of the probe, because of its high mechanical strength even with the small diameters that can be realized with the invention.

The probe tip is cut off at 67 by the film layers, so that radiant energy, e.g., light, radiated from the probe shaft through support 60, issues to the outside through the support surface exposed by the surface of the cut. The light issues only at this point from support 60, since the other parts of the surface of the probe support act as reflectors, due to the reflecting properties of the inner film 61 and also by suitable pairing of the indices of refraction with an additional film arranged directly on the support surface. The radiant energy thus heats only the volume of the tissue directly in front of surface 67. Thus, only a volume tissue which is arranged in the immediate proximity of the ring-shaped thermocouple 66 is thermally influenced, but not the thermocouple 65, which is arranged further back on the shaft.

Figure 2:
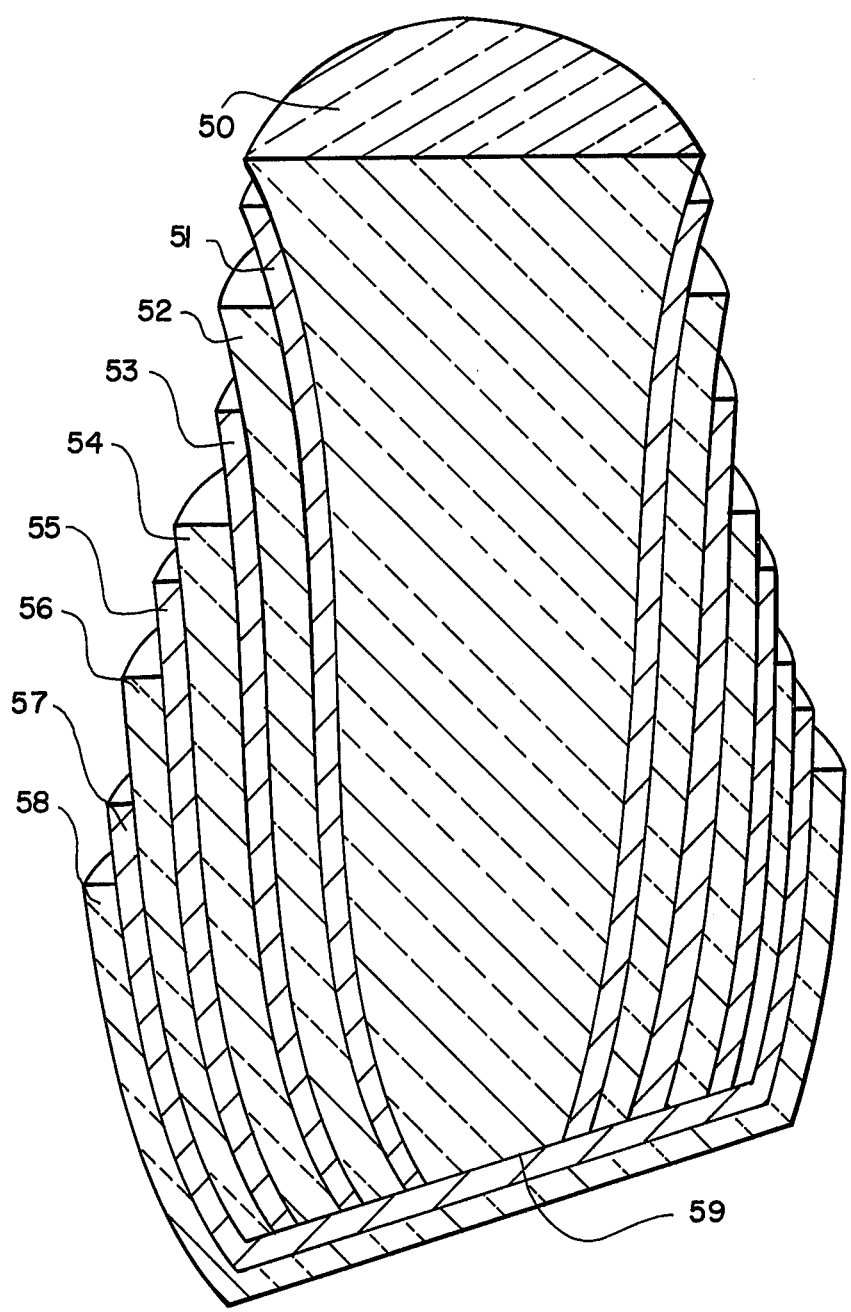
FIG. 2 is a view, similar to FIG. 1, of another embodiment of the invention.

The probe, according to FIG. 2, has, on an insulation support 50, superposed conductor thin films or layers 51, 53, 55 and 57, which are separated by insulating films or layers 52, 54 and 56. The entire arrangement is covered by an additional insulating film 58. After the films 51 to 56 have been applied, the entire arrangement is cut off in the tip area in a surface of cut 59 so that the conductor film 57 applied subsequently contacts the surfaces of cut of all underlying conductor films 51, 53 and 55.

Any two of the conductor films 51, 53, 55 or 57 are designed as a leg and connecting leg of the thermocouple of the tip area, while the other two conductor films form the heating legs of the mutual type thermocouple formed with this arrangement and which consist of four films. The connecting leg passes over into an outwardly extending thermocouple leg in a zone (not shown) in an unheated thermocouple arranged farther back on the shaft.

The outwardly applied insulating layer 58 serves not only as a corrosion protection, but primarily, as thermal resistance to reduce the heating and cooling power to be expended, which is required to maintain a certain over- or under-temperature.

Figure 3:
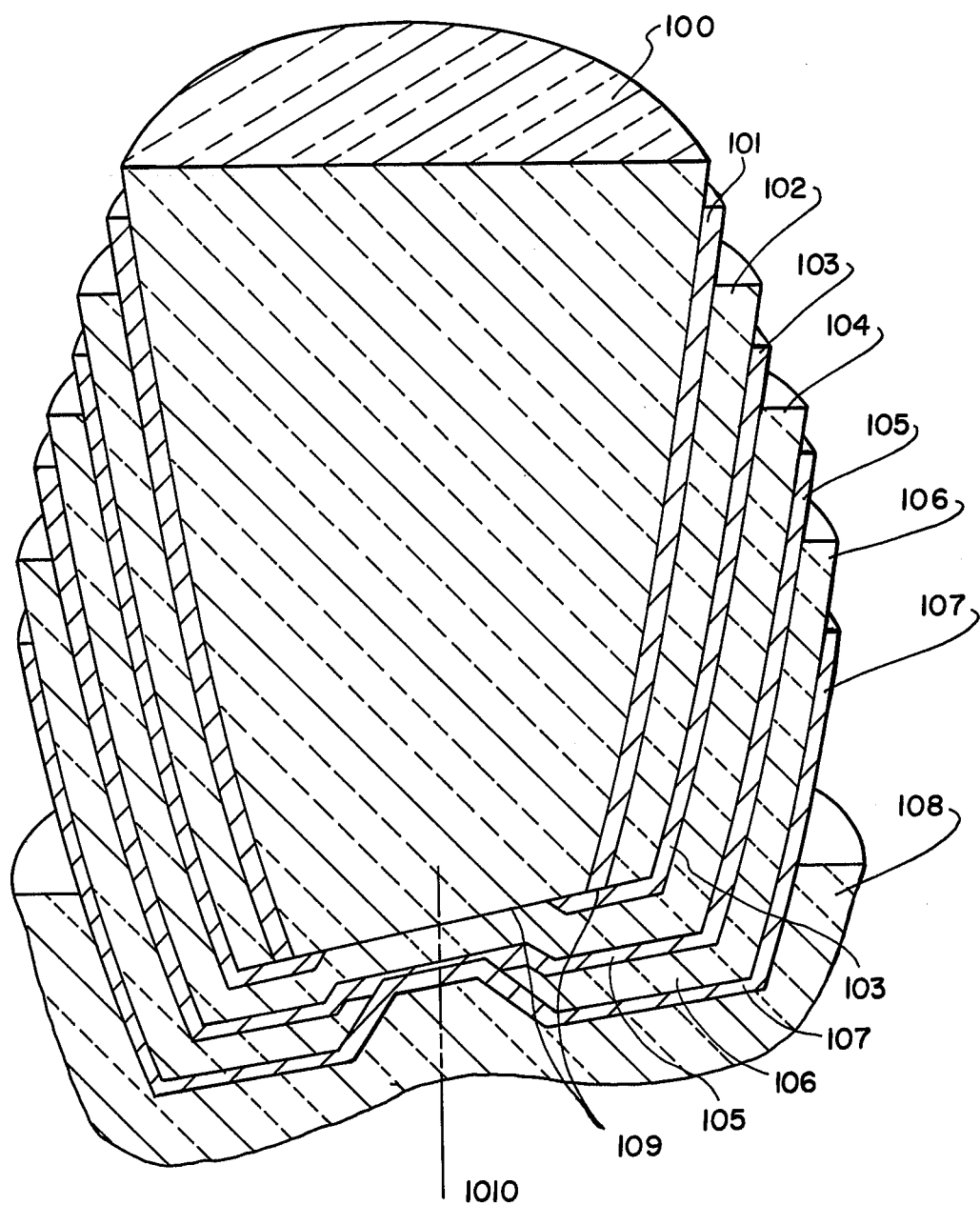
FIG. 3 is a view, similar to FIG. 1, of still another embodiment of the invention with resistance film heating.

The probe, according to FIG. 3, has on a support 100, a first thermocouple conductor film 101 extending from the inside to the outside, an insulating film 102, a second thermoconductor film 103, an insulating film 104, a connecting conductor film 105 for heating, an insulating film 106, and a resistance film 107. Above it is applied an additional insulating film 108 which serves the same purposes as film 58 in FIG. 2.

After films 101 and 102 have been applied, the probe tip is broken off in a surface 109, and the probe shaft and the surface 109 are coated with the second thermocouple conductor film. In the surface of cut 109, the contact of the thermocouple is thus established in ring form.

The second conductor film 103 subsequently applied at the front on surface 109 is removed in a recess around the axis 1010; and the insulating film 104, the connecting film 105, and the insulating film 106, are applied. Then a smaller recess is produced in insulating film 106 around axis 1010, in which the subsequently applied resistance film 107 makes contact with the connecting film 105.

In this probe, the filament power is produced substantially only in the zone directly around the recess or hole in the tip and, thus, in the immediate proximity of the heated thermocouple. The contacting of the outer resistance film 107 with an additional outside connecting conductor (not shown) can take place in a zone of the probe farther back, in which not much filament power is expended, because the support is much thicker there and the conductive cross-section of the resistance film 107 is therefore much greater. The unheated thermocouple (not shown) is also arranged on the shaft of the probe.

In a variation (not shown) of the embodiment in FIG. 3, the heating can also be effected by electric heating of the tissue in front of the probe tip. To this end, the probe represented in FIG. 3 is so designed that the thermocouple conductor 103 passes in front of the probe tip, and the films 104 to 107 are omitted. A hole or recess is provided short of the probe tip in the outer insulating film 108 around the axis 1010, which exposes the surface of film 103. Film 103 is connected, not only to the thermocouple amplifier, but also to a heating current generator to which is also connected a large-surfaced thin film electrode arranged on the probe shaft. A current flows between the electrodes which heats the tissue, and which has a cross-section which is concentrated in front of the small electrode surface in the probe tip and then heats the tissue in front of it with the major part of the filament power.

In another embodiment, the probe tip, according to FIG. 3, can be operated with radiant heat. In the hole or recess around axis 1010, the reflecting film 103 which covers the probe, is missing in the surface 109. Radiant energy conducted through support 100 to the probe tip can issue in this hole from the support and be absorbed in the overlying film structure. This probe is characterized again by a very simple layered structure.

Figure 4:
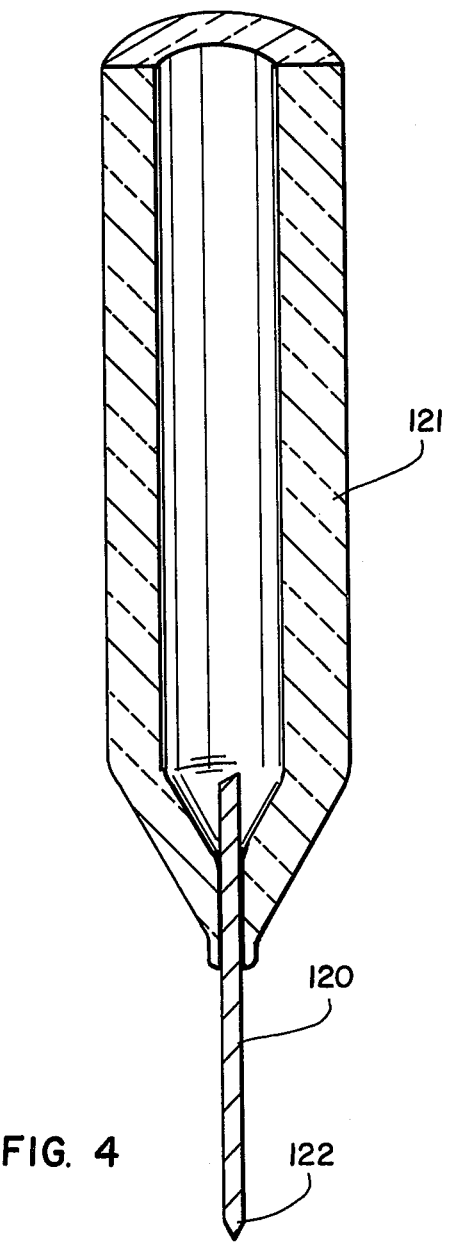
FIG. 4 is a view of another embodiment of probe on a much smaller scale and having a fiber tip.

FIG. 4 shows a support whose tip and shaft do not consist of the same material but which has a shaft tube support 121 and an inorganic fiber 120 as a probe tip. This fiber 120 can be a whisker, for example, or a polycrystalline fiber, or a bundle of fibers. These fibers have great physical properties.

Fiber 102 is secured in the tip of the shaft tube 121. It has, for example, a diameter of a few μ, and is coated during the subsequent application of the layered structure of the probe together with the shaft tube 121 with the layers. The measuring arrangement is provided on the extremely fine, preferably additionally pointed, fiber tip 120, while the contacting of the conductor film with connecting wires, is effected on shaft tube 121 in a zone farther back.

In such a probe with fiber tip, the diameter of the probe is extremely small in the part formed by the fiber up to a considerable distance from the probe tip. In this way, changes in the blood circulation caused by the probe are avoided in the measuring range.

While specific embodiments of the invention have been shown and described in detail to illustrate the application of the principles of the invention, it will be understood that the invention may be embodied otherwise without departing from such principles.

What is claimed is:

1. A puncture probe for measuring heat transfer or blood circulation of living tissues, particularly in man, comprising a probe support having a tip, first and second oppositely connected thermocouples each formed of an outwardly extending layer of a thermoelectric material and of a common connecting layer of a different thermoelectric material, one of said thermocouples being heated and arranged in the range of said probe tip, the other of said thermocouples being unheated and arranged at a spaced location on said probe support, said first thermocouple having an outwardly extending layer arranged in the vicinity of said tip and a connecting layer comprising a plurality of superposed thin conductor films separated by insulating thin films except in an area forming a contact zone between said conductive films on the surface of said support probe, said second thermocouple having an outwardly extending layer comprising a thin conductive film contacting said connecting layer.

2. A puncture probe, according to claim 1, including a thin resistance film for heating the heated thermocouple extending over said films on said probe and separated from said thermocouple by an insulating film.

3. A puncture probe, according to claim 2, including a thin conductor heating current supply film in contact with said resistance film on an extrememly small area within the circular shaped and heated thermocouple and heating current conductor insulating films separating said conductor film from the other conductive layers.

4. A puncture probe, according to claim 1, including two additional thin films of different thermoelectric materials insulated by insulating thin films contacted in a mutual type thermocouple with said heated thermocouple.

5. A puncture probe, according to claim 1, wherein said probe support comprises a radiant heating photoconductor having a surface which forms a reflector at said probe with the exception of a window portion arranged in the zone to be heated.

6. A puncture probe, according to claim 5, including a layered structure absorbing radiant energy arranged above said window.

7. A puncture probe, according to claim 5, wherein said window provides a free passage of the radiation to the absorbent tissue.

8. A puncture probe, according to claim 1, wherein the tissue is heated, comprising two electrodes, one comprising a small electrode arranged in the zone to be heated characterized in that the small electrode is provided with an exposed panel of a conductor thin film arranged on the probe and covered with insulation on its exterior, while the other larger electrode is arranged on the outer surface of said shaft portion of said support.

9. A puncture probe, according to claim 1, wherein said support comprises a fiber.

10. A puncture probe, according to claim 1, wherein at least the heated zone of the probe is coated with a film of low thermal conductivity.

11. A puncture probe for measuring heat transfer or blood circulation of living tissues, particularly in man, comprising an electrically and thermally insulating pointed probe support having an end tip, first and second oppositely connected thermocouples, each comprising a layer of thermoelectric material forming an outwardly extending leg and a common connecting leg of a different thermoelectric material, one thermocouple being heated and disposed on said probe adjacent said tip and the other thermocouple being unheated and spaced from said end tip, said first thermocouple having an extending leg arranged adjacent said end tip and a connecting leg composed of a plurality of superposed thin conductive films separated by insulating films on an area forming a contact zone on the surface of said probe support, said second thermocouple having an outwardly extending leg of a thin film, and a common leg contacting said first thermocouple common leg and being composed of a plurality of superposed thin conductor films separated by insulation films.

* * * * *